United States Patent
Namii et al.

(10) Patent No.: US 9,706,906 B2
(45) Date of Patent: Jul. 18, 2017

(54) ENDOSCOPE OBJECTIVE OPTICAL SYSTEM

(71) Applicant: OLYMPUS CORPORATION, Hachioji-shi, Tokyo (JP)

(72) Inventors: Yasushi Namii, Tokyo (JP); Ikutoshi Fukushima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/225,892

(22) Filed: Aug. 2, 2016

(65) Prior Publication Data

US 2016/0338576 A1    Nov. 24, 2016

Related U.S. Application Data

(63) Continuation of application No. PCT/JP2015/068927, filed on Jun. 30, 2015.

(30) Foreign Application Priority Data

Jul. 9, 2014  (JP) ................................ 2014-141517

(51) Int. Cl.
*A61B 1/00* (2006.01)
*G02B 13/04* (2006.01)
(Continued)

(52) U.S. Cl.
CPC ...... *A61B 1/00193* (2013.01); *A61B 1/00096* (2013.01); *G02B 13/04* (2013.01);
(Continued)

(58) Field of Classification Search
CPC ................................................ A61B 1/00193
(Continued)

(56) References Cited

U.S. PATENT DOCUMENTS

| 4,688,906 A | 8/1987 | Hilbert et al. |
| 5,122,650 A | 6/1992 | McKinley |

(Continued)

FOREIGN PATENT DOCUMENTS

| JP | 62215221 A | 9/1987 |
| JP | 06194581 A | 7/1994 |

(Continued)

OTHER PUBLICATIONS

International Search Report (ISR) and Written Opinion dated Oct. 6, 2015 issued in International Application No. PCT/JP2015/068927.

*Primary Examiner* — Thomas K Pham
*Assistant Examiner* — Mitchell Oestreich
(74) *Attorney, Agent, or Firm* — Holtz, Holtz & Volek PC

(57) ABSTRACT

Provided is a small endoscope objective optical system that allows stereoscopic viewing even though a wide angle is used, that reduces the F-number, and that also reduces vignetting.
Provided is an endoscope objective optical system that consists of, sequentially from the object side, a negative first lens group, a positive second lens group, and a pair of third lens groups that are disposed side-by-side in the direction of parallax and that form two optical images with parallax, wherein aperture stops are individually provided in the third lens groups, and conditional expression M below is satisfied:

$$Fob\_n/Fob\_p > -0.5 \qquad (1),$$

where $Fob\_n$ is a focal length of the first lens group, and $Fob\_p$ is a focal length of the second lens group.

4 Claims, 6 Drawing Sheets

(51) Int. Cl.
*G02B 23/26* (2006.01)
*G02B 23/24* (2006.01)

(52) U.S. Cl.
CPC ....... *G02B 23/243* (2013.01); *G02B 23/2415* (2013.01); *G02B 23/26* (2013.01)

(58) Field of Classification Search
USPC ......................................................... 359/656
See application file for complete search history.

(56) References Cited

U.S. PATENT DOCUMENTS

| | | | |
|---|---|---|---|
| 5,191,203 A | 3/1993 | McKinley | |
| 5,496,261 A * | 3/1996 | Sander | G02B 23/2438 359/379 |
| 5,673,147 A | 9/1997 | McKinley | |
| 5,689,365 A | 11/1997 | Takahashi | |
| 2009/0096865 A1* | 4/2009 | McKinley | G02B 23/2415 348/45 |
| 2014/0239206 A1 | 8/2014 | Namii et al. | |

FOREIGN PATENT DOCUMENTS

| | | |
|---|---|---|
| JP | 06509425 A | 10/1994 |
| JP | 06331937 A | 12/1994 |
| JP | 07236610 A | 9/1995 |
| JP | 08082766 A | 3/1996 |
| JP | 11503844 A | 3/1999 |
| JP | 2014140593 A | 8/2014 |
| WO | 9219008 A1 | 10/1992 |
| WO | 9633436 A1 | 10/1996 |
| WO | 2013114725 A1 | 8/2013 |
| WO | 2014038397 A1 | 3/2014 |
| WO | 2015119007 A1 | 8/2015 |

* cited by examiner

ENDOSCOPE OBJECTIVE OPTICAL SYSTEM

CROSS-REFERENCE TO RELATED APPLICATIONS

This is a continuation of International Application PCT/JP2015/068927 which is hereby incorporated by reference herein in its entirety.

This application is based on Japanese Patent Application No. 2014-141517, the contents of which are incorporated herein by reference.

TECHNICAL FIELD

The present invention relates to an objective optical system, and relates, in particular, to an endoscope objective optical system employed in a medical endoscope.

BACKGROUND ART

In the related art, objective optical systems for performing stereoscopic viewing by forming two optical images with parallax on a single image-acquisition element have been proposed.

As an example of such an objective optical system, Patent Literature 1 discloses an objective optical system provided with, sequentially from the object side, a front-group optical system shared between the left and right (in two directions of parallax) and a pair of, that is, left and right, imaging optical systems.

CITATION LIST

Patent Literature

{PTL 1} Japanese Unexamined Patent Application, Publication No. Hei 8-82766

SUMMARY OF INVENTION

Solution to Problem

An aspect of the present invention provides an endoscope objective optical system that consists of, sequentially from the object side, a negative first lens group, a positive second lens group, and a pair of third lens groups that are disposed side-by-side in a direction of parallax and that form two optical images with parallax, wherein aperture stops are individually provided in the third lens groups, and conditional expression (1) below is satisfied:

$$Fob\_n/Fob\_p > -0.5 \tag{1},$$

where $Fob\_n$ is a focal length of the first lens group, and $Fob\_p$ is a focal length of the second lens group.

DESCRIPTION OF EMBODIMENT

First Embodiments

An endoscope objective optical system according to first embodiment of the present invention, will be described below with reference to the drawings.

Figure 1:
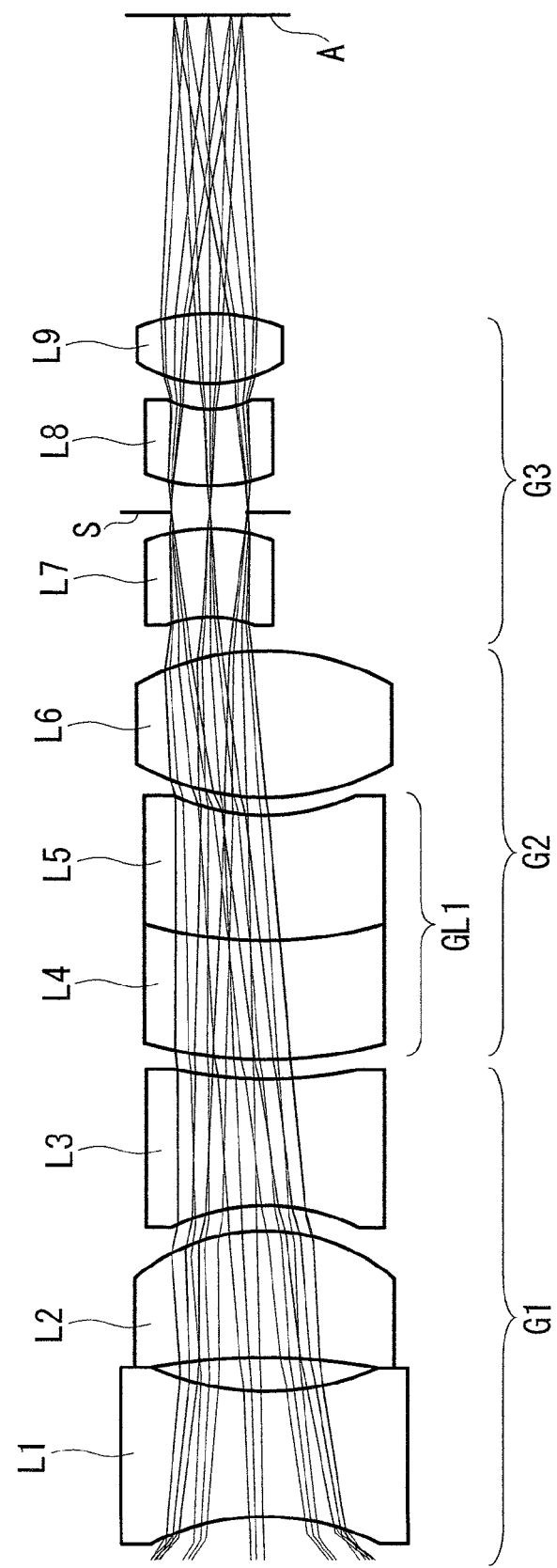
FIG. 1 is a cross-sectional view showing the overall configuration of an endoscope objective optical system according to a first embodiment of the present invention.

FIG. 1 shows a cross-sectional view showing the overall configuration of the endoscope objective optical system. As shown in FIG. 1, the endoscope objective optical system is provided with a plurality of lens groups sequentially from the object side, namely, a negative first lens group G1, a positive second lens group G2, and a pair of third lens groups G3 that are disposed side-by-side in a direction of parallax and that form two optical images with parallax. Note that, in this embodiment, only one of the pair of optical systems of the third lens groups G3 disposed in the direction of parallax is illustrated for the sake of convenience of explanation.

The first lens group is provided with, sequentially from the object side, a first lens L1, a second lens L2, and a third lens L3, and has negative optical power as a whole.

The second lens group G2 consists of, sequentially from the object side, a cemented lens CL1, formed between a fourth lens L4 and a fifth lens L5, and a sixth lens L6, and has positive optical power as a whole.

The third lens groups G3 are disposed side-by-side in the direction of parallax, individually focus light entering from the imaging subject via the first lens group G1 and the second lens group G2, and make the focused light incident on a light-receiving surface A of an image-acquisition element. Each of the third lens groups G3 consists of, sequentially from the object side, a seventh lens L7, an aperture stop S, an eighth lens L8, and a ninth lens L9. In FIG. 1, only one of the two third lens groups G3 is shown, and the other is omitted from the illustration.

In addition, the endoscope objective optical system according to this embodiment is configured so as to satisfy the following conditional expression (1):

$$Fob\_n/Fob\_p > -0.5 \tag{1},$$

where $Fob\_n$ is the focal length of the first lens group G1, and $Fob\_p$ is the focal length of the second lens group G2.

Conditional expression (1) defines conditions related to a ratio between the focal length of the first lens group G1 and the focal length of the second lens group G2, and, by decreasing the focal length of the first lens group G1, it is possible to form a wide-angle endoscope objective optical system in which the total angle is equal to or greater than 90°. In addition, by individually providing the aperture stops in the third lens groups G3, it is possible to reduce the beam-bundle diameters in the third lens groups G3, and thus, it is possible to achieve stereoscopic viewing even though a wide angle is used, and it is possible to reduce the F-number and also to reduce vignetting.

In the case in which conditional expression (1) is not satisfied, the negative power due to the first lens group G1 and the second lens group G2 is reduced. Because of this, in order to satisfy the wide-angle conditions, it is necessary to position the third lens groups G3 at positions farther away from the optical axes of the first lens group G1 and the second lens group G2 in the direction of parallax, or it is necessary to expand the beam bundles traveling from the seventh lenses L7 of the third lens groups G3 to the sixth lens L6 of the second lens group G2. However, because in both cases, the beam-bundle diameter at the sixth lens L6 is increased, the size of the lens system as a whole is increased, and, furthermore, it is necessary to correct aberrations at a position far away from the lens center of the second lens group G2, thus making it difficult to achieve a performance level that is compatible with the high pixel counts.

In addition, the endoscope objective optical system is configured so as to satisfy conditional expression (2)

$$fs/fb < 2.5 \qquad (2),$$

where fs is the distance from the position of the aperture stop S to the imaging surface (light-receiving surface A), and fb is the distance from the ninth lens L9, which is the final lens, to the imaging surface.

Conditional expression (2) defines the range within which the aperture stops S are positioned, and, it is possible to further reduce the beam-bundle diameters by disposing the aperture stops S within the range of conditional expression (2).

In the case in which conditional expression (2) is not satisfied, because the distances from the aperture stops S to the imaging surface are increased, the beam-bundle diameters end up becoming large in the eighth lenses L8 and the ninth lenses L9 of the third lens groups G3. Therefore, in the third lens groups G3, vignetting occurs in the beam bundles, and thus, it becomes difficult to make the optical system compatible with a high pixel count.

As has been described, with this embodiment, it is possible to form a wide-angle endoscope objective optical system in which the total angle is equal to or greater than 90° by decreasing the focal length of the first lens group G1; it is possible to reduce the beam-bundle diameter in each of the third lens groups G3 by disposing the aperture stop S in the predetermined area of the each of the third lens groups G3; stereoscopic viewing is possible even though a wide angle is used; and it is possible to reduce the F-number and to reduce vignetting.

Second Embodiment

In addition, as a second embodiment of the present invention, it is possible to configure an endoscope objective optical system as follows.

Figure 2:
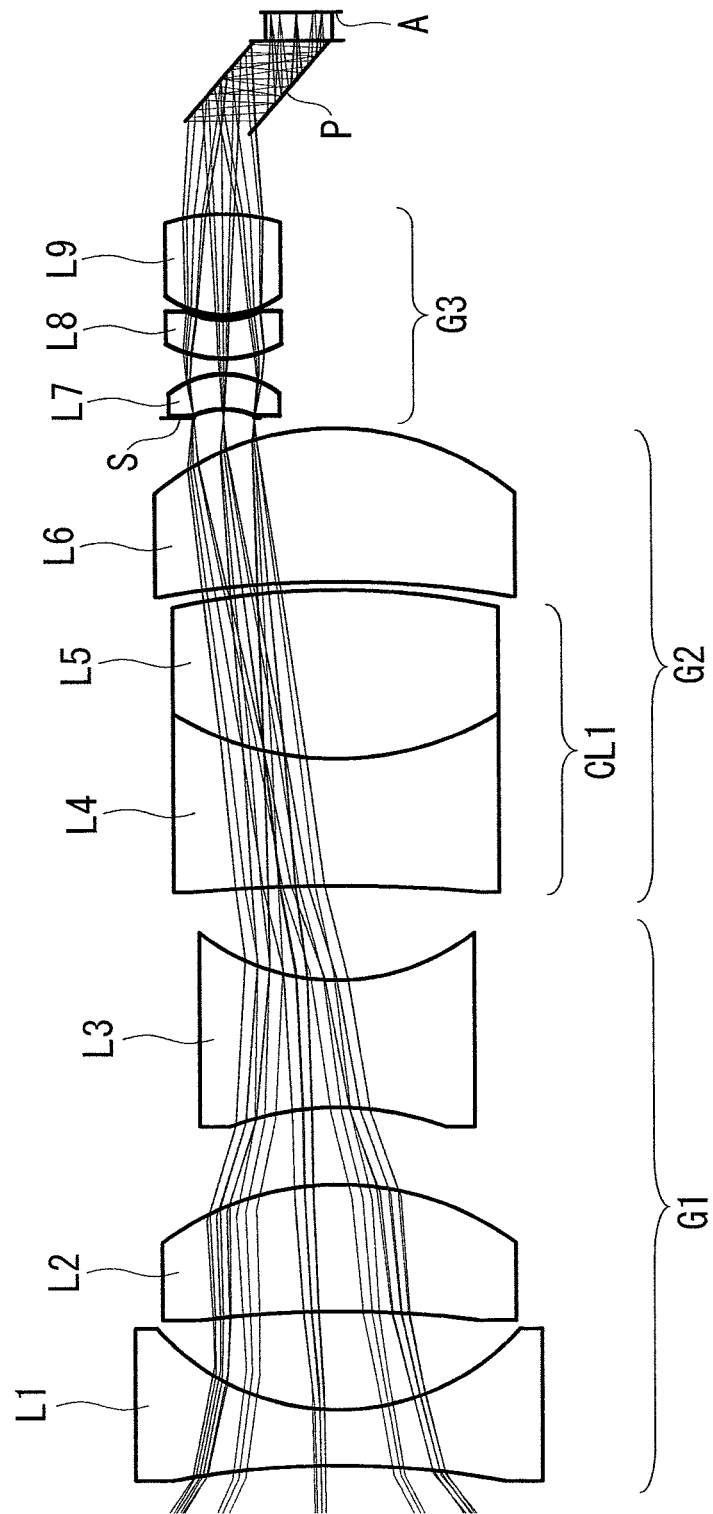
FIG. 2 is a cross-sectional view showing the overall configuration of an endoscope objective optical system according to a second embodiment of the present invention.

As shown in FIG. 2, an endoscope objective optical system according to this embodiment consists of, sequentially from the object side, the negative first lens group G1, the positive second lens group G2, the pair of third lens groups G3 that are disposed side-by-side in the direction of parallax and that form two optical images with parallax, and reflection optical systems P having two reflection surfaces. In other words, the reflection optical systems P are provided between the third lens groups G3 and the imaging surface A. In addition, in this e diment, the aperture stops S are disposed on the object side of the seventh lenses L7, which are the lenses that are closest to the object side in the third lens groups G3.

In addition, the endoscope objective optical system according to this embodiment is configured so as to satisfy conditional expression (3) below, in addition to the above-described conditional expressions (1) and (2):

$$fb/ihy > 4 \qquad (3),$$

where fb is the distance from the ninth lens L9, which is the final lens, to the imaging surface A, and ihy is the maximum image height in the direction of parallax.

By employing the reflection optical systems P having the two reflection surfaces, it is possible to form two optical images with parallax on a single image-acquisition element so as to be closer to each other, and, by satisfying conditional expression. (3), it is possible to prevent the occurrence of vignetting in the beam bundles in the reflection optical systems P.

EXAMPLES

Next, Examples 1 to 4 of the endoscope objective optical systems according to one of the above-described embodiments will be described with reference to FIGS. 3 to 6. In lens data described in the Example sections, r is the radius of curvature (unit: mm), d is the surface interval (mm), Ne is the refractive index with respect to the e-line, and vd is the Abbe number with respect to the d-line.

Example 1

Figure 3:
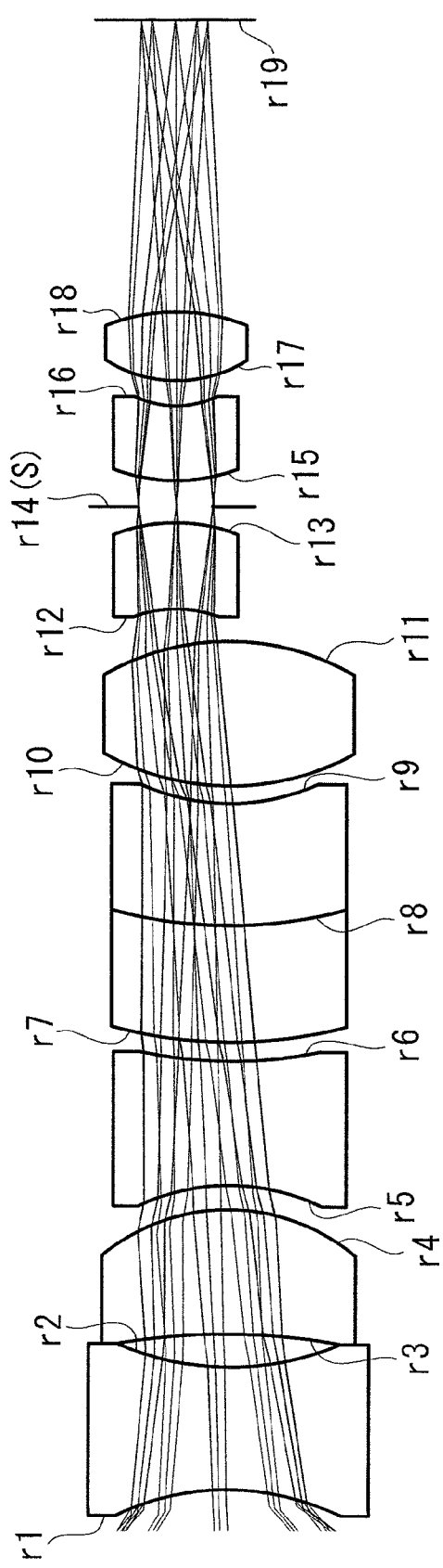
FIG. 3 is a cross-sectional view showing the overall configuration of an endoscope objective optical system according to an example of the first embodiment of the present invention.

FIG. 3 is a cross-sectional view showing the overall configuration of an endoscope objective optical system according to an Example of the first embodiment.

The endoscope objective optical system according to Example 1 consists of, sequentially from the object side, a negative first lens group, a positive second lens group, and a pair of third lens groups that are arranged in the direction of parallax. In addition, the aperture stops S are disposed on the image-surface sides of lenses disposed closest to the object sides of the third lens groups.

Lens data of the endoscope objective optical system according to this Example 1 are shown below.

Lens Data

| Surface Number | r | d | Ne | vd |
| --- | --- | --- | --- | --- |
| Object Surface |  | 15 |  |  |
| 1 | −3.80837 | 1.5 | 1.883 | 40.7645 |
| 2 | 4.14645 | 0.400822 |  |  |
| 3 | −9.69475 | 1.50498 | 1.76182 | 26.5174 |
| 4 | −2.85208 | 0.288 |  |  |
| 5 | −3.27565 | 1.50498 | 1.63854 | 55.3792 |
| 6 | 6.22293 | 0.226368 |  |  |
| 7 | 6.83208 | 1.41587 | 1.84666 | 23.7775 |
| 8 | 6.75522 | 1.46717 | 1.7495 | 35.3319 |
| 9 | 3.18333 | 0.214991 |  |  |
| 10 | 3.73937 | 1.72575 | 1.603 | 65.4427 |
| 11 | −3.71946 | 0.392832 |  |  |
| 12 | −1.7681 | 1.04509 | 1.54072 | 47.2264 |
| 13 | −2.48904 | 0.209019 |  |  |
| 14 (Aperture stop) |  | 0.298598 |  |  |
| 15 | 2.5571 | 0.895795 | 1.92286 | 18.8966 |
| 16 | 1.45226 | 0.298598 |  |  |
| 17 | 1.98468 | 0.82944 | 1.62041 | 60.2887 |
| 18 | −3.11608 | 3.503161 |  |  |
| 19 (Image Surface) |  |  |  |  |

Miscellaneous Data
Focal length Fob_n of the first lens group −1.4266 mm
Focal length Fob_p of the second lens group 5.60043 mm
Distance fs from the imaging surface to the aperture stop 5.8256 mm
Distance fb from the final lens to the imaging surface 3.503161 mm
Maximum image height ihy in the direction of parallax 0.45 mm
Amounts of displacement between the optical axis of the third lens group and the optical axes of the first and second lens groups 0.72 mm
F-number 4
Angle of view 59.9433°
Fob_n/Fob_p −0.25473044
fs/fb 1.662955257
fb/ihy 7.784802222

Example 2

Figure 4:
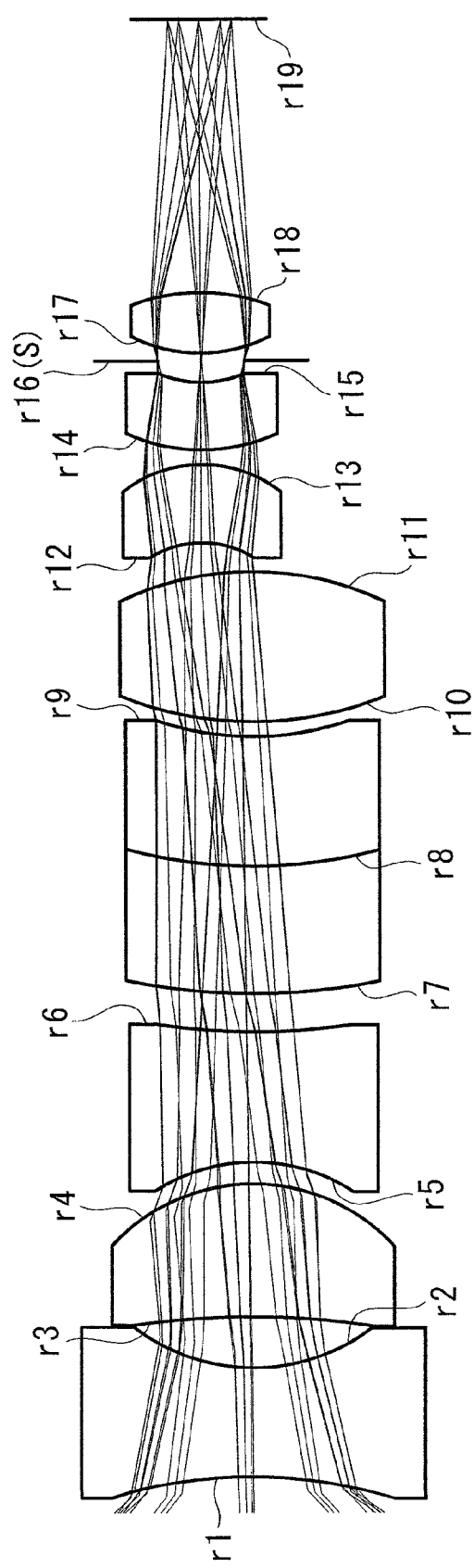
FIG. 4 is a cross-sectional view showing the overall configuration of an endoscope objective optical system according to another example of the first embodiment of the present invention.

FIG. 4 is a cross-sectional view showing the overall configuration of an endoscope objective optical tem according to another Example of the first embodiment.

The endoscope objective optical system according to this Example consists of, sequentially from the object side, a negative first lens group, a positive second lens group, and a pair of third lens groups that are arranged in the direction of parallax. In addition, the aperture stops S are disposed at the object sides of lenses disposed closest to the image-surface sides of the third lens groups.

Lens data of the endoscope objective optical system according to this Example 2 are shown below.
Lens Data

| Surface Number | r | d | Ne | vd |
|---|---|---|---|---|
| Object Surface | | 15 | | |
| 1 | −6.95702 | 1.5 | 1.883 | 40.7645 |
| 2 | 2.98074 | 0.689341 | | |
| 3 | −11.5723 | 1.7935 | 1.76182 | 26.5174 |
| 4 | −2.83423 | 0.288 | | |
| 5 | −2.74912 | 1.7935 | 1.63854 | 55.3792 |
| 6 | 11.0428 | 0.514887 | | |
| 7 | 10.0787 | 1.70439 | 1.84666 | 23.7775 |
| 8 | 7.26287 | 1.75569 | 1.7495 | 35.3319 |
| 9 | 4.59815 | 0.214991 | | |
| 10 | 5.33836 | 2.01427 | 1.603 | 65.4427 |
| 11 | −4.52516 | 0.392832 | | |
| 12 | −1.47378 | 1.04509 | 1.54072 | 47.2264 |
| 13 | −2 | 0.209019 | | |
| 14 | 2.70984 | 0.895795 | 1.92286 | 18.8966 |
| 15 | 1.49409 | 0.298598 | | |
| 16 (Aperture stop) | | 0.1 | | |
| 17 | 2.19475 | 0.82944 | 1.62041 | 60.2887 |
| 18 | −2.97994 | 3.68799 | | |
| 19 (Image Surface) | | | | |

Focal length Fob_n of the first lens group −1.61395 mm
Focal length Fob_p of the second lens group 7.10026 mm
Distance fs from the imaging surface to the aperture stop 4.61743 mm
Distance fb from the final lens to the imaging surface 3.68799 mm
Maximum image height ihy in the direction of parallax 0.45 mm
Amounts of displacement between the optical axis of the third lens group and the optical axes of the first and second lens groups 0.72 mm
F-number 3
Angle of view 59.9961°
Fob_n/Fob_p −0.227308577
f /fb 1.252018037
fb/ihy 8.195533333

Example 3

Figure 5:
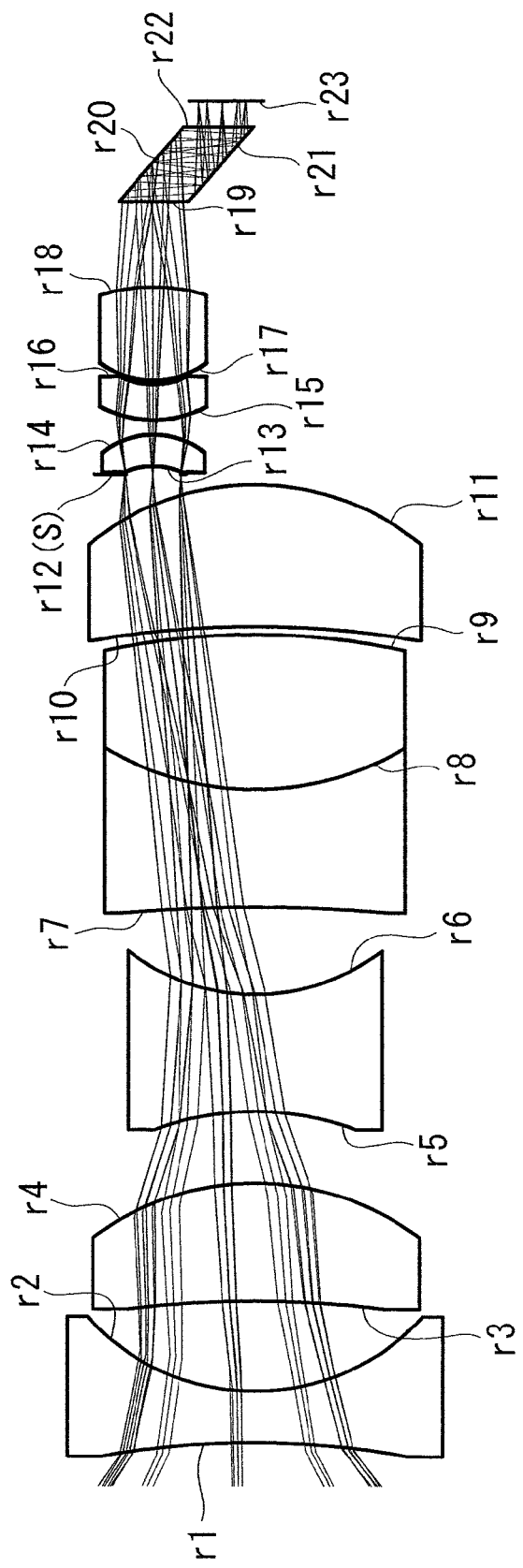
FIG. 5 is a cross-sectional view showing the overall configuration of an endoscope objective optical system according to an example of the second embodiment of the present invention.

FIG. 5 is a cross-sectional view showing the overall configuration of an endoscope objective optical system according to an Example of the second embodiment.

The endoscope objective optical system according to this Example consists of, sequentially from the object side, a negative first lens group, a positive second lens group, a pair of third lens groups that are arranged in the direction parallax, and reflection optical systems having two reflection surfaces. In addition, the aperture stops S are disposed at the object sides of lenses disposed closest to the object sides of the third lens groups.

Lens data of the endoscope objective optical system according to this Example 3 are shown bellow.
Lens Data

| Surface Number | r | d | Ne | vd |
|---|---|---|---|---|
| Object Surface | | 15 | | |
| 1 | −12.5697 | 0.6 | 1.883 | 40.7645 |
| 2 | 3.12377 | 1.04167 | | |
| 3 | −15.47 | 1.36097 | 1.92286 | 18.8966 |
| 4 | −3.84137 | 0.801512 | | |
| 5 | −4.20218 | 1.36097 | 1.63854 | 55.3792 |
| 6 | 2.89504 | 1.00414 | | |
| 7 | −19.4523 | 1.33611 | 1.84666 | 23.7775 |
| 8 | 4.08815 | 1.78599 | 1.7495 | 35.3319 |
| 9 | −11.1098 | 0.1 | | |
| 10 | −14.0755 | 1.6083 | 1.603 | 65.4427 |
| 11 | −3.71871 | 0.12 | | |
| 12 (Aperture stop) | | 0.1 | | |
| 13 | −1.00081 | 0.35 | 1.78472 | 25.683 |
| 14 | −1.19388 | 0.17 | | |
| 15 | 1.59833 | 0.4 | 1.92286 | 18.8966 |
| 16 | 1.05853 | 0.05 | | |
| 17 | 1.22734 | 1.08349 | 1.51633 | 64.1411 |
| 18 | −2.30257 | 0.965003 | | |
| 19 | ∞ | 0.45 | 1.51633 | 64.1411 |
| 20 | ∞ (Reflection Surface) | 0.9 | 1.51633 | 64.1411 |
| 21 | ∞ (Reflection Surface) | 0.4 | 1.51633 | 64.1411 |
| 22 | ∞ | 0.3 | | |
| 23 (Image Surface) | | | | |

Miscellaneous Data
Focal length Fob_n of the first lens group −1.36547 mm
Focal length Fob_p of the second lens group 6.93611 mm
Distance fs from the imaging surface to the aperture stop 5.16849 mm
Distance fb from the final lens to the imaging surface fb 3.015003 mm
Maximum image height ihy in the direction of parallax 0.3 mm
Amounts of displacement between the optical axis of the third lens group and the optical axes of the first and second lens groups 1.3 mm F-number 3.5
Angle of view 47°
Fob_n/Fob_p −0.196863948
fs/fb 1.714257001
fb/ihy 10.05001

Example 4

Figure 6:
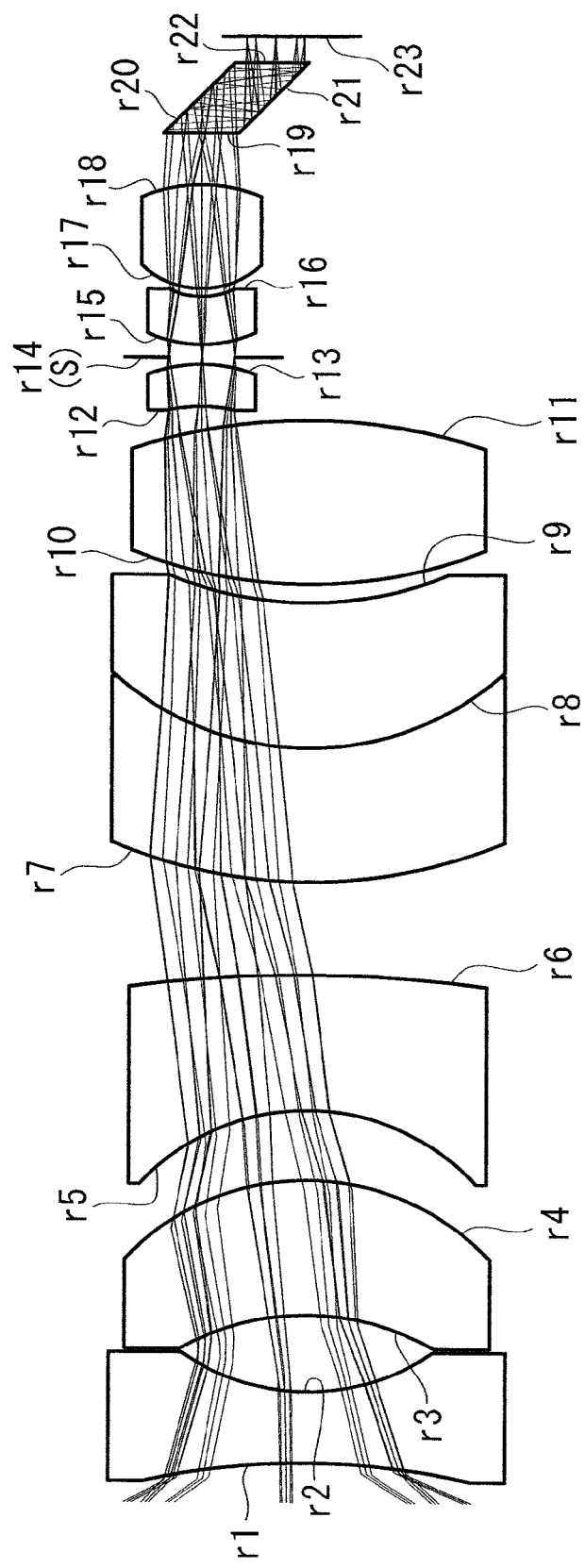
FIG. 6 is a cross-sectional view showing the overall configuration of an endoscope objective optical system according to another example of the second embodiment of the present invention.

FIG. 6 is a cross-sectional view showing the overall configuration of an endoscope objective optical system according to another Example of the second embodiment.

The endoscope objective optical system according to this Example consists of, sequentially from the object side, a negative first lens group, a positive second lens group, and a pair of third lens groups that are arranged in the direction of parallax, and reflection optical systems having two reflection surfaces. In addition, the aperture stops S are disposed at the image-surface sides of lenses disposed closest to the object sides of the third lens groups.

Lens data of the endoscope objective optical system according to this Example 4 are shown below.

Lens Data

| Surface Number | r | d | Ne | vd |
|---|---|---|---|---|
| Object Surface | | 15 | | |
| 1 | −8.92789 | 0.864 | 1.883 | 40.7645 |
| 2 | 2.72124 | 0.953406 | | |
| 3 | −3.02092 | 1.64979 | 1.92286 | 18.8966 |
| 4 | −2.99104 | 0.844168 | | |
| 5 | −2.80703 | 1.64979 | 1.63854 | 55.3792 |
| 6 | −15.6192 | 1.13595 | | |
| 7 | 6.11084 | 1.61398 | 1.84666 | 23.7775 |
| 8 | 3.56736 | 1.79002 | 1.7495 | 35.3319 |
| 9 | 4.60374 | 0.2 | | |
| 10 | 5.72221 | 2.00594 | 1.603 | 65.4427 |
| 11 | −6.89945 | 0.17 | | |
| 12 | −1.50531 | 0.504 | 1.78472 | 25.683 |
| 13 | −1.77592 | 0.1008 | | |
| 14 (Aperture stop) | | 0.144 | | |
| 15 | 1.51588 | 0.576 | 1.92286 | 18.8966 |
| 16 | 0.903019 | 0.1 | | |
| 17 | 1.06837 | 1.25022 | 1.51633 | 64.1411 |
| 18 | −1.94052 | 0.645411 | | |
| 19 | ∞ | 0.45 | 1.51633 | 64.1411 |
| 20 | ∞ (Reflection Surface) | 0.9 | 1.51633 | 64.1411 |
| 21 | ∞ (Reflection Surface) | 0.4 | 1.51633 | 64.1411 |
| 22 | ∞ | 0.3 | | |
| 23 (Image Surface) | | | | |

Miscellaneous Data

Focal length Fob_n of the first lens group −1.62639 mm
Focal length Fob_p of the second lens group 7.69043 mm
Distance Fs from the imaging surface to the aperture stop 4.76563 mm
Distance Fb from the final lens to the imaging surface 2.695411 mm
Maximum image height ihy in the direction of parallax 0.35 mm
Amounts of displacement between the optical axis of the third lens group and the optical axes of the first and second lens groups 1.3 mm
F-number 3.5
Angle of view 700116°
Fob_n/Fob_p −0.211482323
fs/fb 1.768053184
fb/ihy 7.701174286

Table 1 shows values related to the above-described conditional expressions (1) to (3) in the above-described Examples 1 to 4.

TABLE 1

| | Example 1 | Example 2 | Example 3 | Example 4 |
|---|---|---|---|---|
| Conditional expression (1) Fob_n/Fob_p > −0.5 | −0.25473044 | −0.227308577 | −0.196863948 | −0.211482323 |
| Conditional expression (2) fs/fb < 2.5 | 1.662955257 | 1.252018037 | 1.714257001 | 1.768053184 |
| Conditional expression (3) fb/ihy > 4 | 7.784802222 | 8.195533333 | 10.05001 | 7.701174286 |

The above-described embodiment leads to the following inventions.

An aspect of the present invention provides an endoscope objective optical system that consists of, sequentially from the object side, a negative first lens group, a positive second lens group, and a pair of third lens groups that are disposed side-by-side in a direction of parallax and that form two optical images with parallax, wherein aperture stops are individually provided in the third lens groups, and conditional expression (1) below is satisfied:

$$Fob\_n/Fob\_p > -0.5 \quad (1),$$

where Fob_n is a focal length of the first lens group, and Fob_p is a focal length of the second lens group.

In this aspect, conditional expression (1) defines conditions related to a ratio between the focal length of the first lens group and the focal length of the second lens group, and, by decreasing the focal length of the first lens group, it is possible to form a wide-angle objective optical system in which the total angle is equal to or greater than 90°. In addition, by individually providing the aperture stops in the third lens groups, because it is possible to reduce the beam-bundle diameters in the third lens groups, it is possible to achieve stereoscopic viewing even though a wide angle is used, and it is possible to reduce the F-number and also to reduce vignetting.

In, the above-described aspect, it is preferable that conditional expression (2) below be satisfied:

$$fs/fb < 2.5 \quad (2),$$

where fs is a distance from a position of the aperture stop to an imaging surface, and fb is a distance from a final lens to the imaging surface.

By setting the position of the aperture stop within the range of conditional expression (2) in this way, it is possible to further reduce the beam-bundle diameter.

In addition, in the above-described aspect, it is preferable that reflection optical systems having two reflection surfaces be individually disposed between the third lens groups and the imaging surface.

By employing the reflection optical systems having two reflection surfaces in this way, it becomes possible to form two optical images with parallax on a single image-acquisition element so as to be closer to each other.

In addition, in the above-described aspect, it is preferable that conditional expression (3) below be satisfied:

$$fb/ihy>4 \qquad (3),$$

where fb is a distance from a final lens to an imaging surface, and ihy is a maximum image height in the direction of parallax.

By doing so, it is possible to prevent the occurrence of vignetting in beam bundles in the reflection optical systems.

REFERENCE SIGNS LIST

G1 first lens group
G2 second lens group
G3 third lens group
P reflection, optical system
S aperture stop
L1 first lens
L2 second lens
L3 third lens
L4 fourth lens
L5 fifth lens
L6 sixth lens
L7 seventh lens
L8 eighth lens
L9 ninth lens
CL1 cemented lens

The invention claimed is:

1. An endoscope objective optical system that consists of, sequentially from the object side, a negative first lens group having a single central axis, a positive second lens group having a single central axis, and a pair of third lens groups that are disposed side-by-side in a direction of parallax and that form two optical images with parallax, wherein the negative first lens group consists of, sequentially from the object side, a negative lens, a positive lens, and a negative lens;

wherein the positive second lens group consists of, sequentially from the object side, a cemented lens and a positive lens; and wherein aperture stops are individually provided in the third lens groups, and conditional expression (1) below is satisfied:

$$Fob\_n/Fob\_p>-0.5 \qquad (1),$$

where Fob_n is a focal length of the first lens group, and Fob_p is a focal length of the second lens group.

2. An endoscope objective optical system according to claim 1 that satisfies conditional expression (2) below:

$$fs/fb<2.5 \qquad (2),$$

where fs is a distance from a position of the aperture stop to an imaging surface, and fb is a distance from a final lens to the imaging surface.

3. An endoscope objective optical system according to claim 1, wherein reflection optical systems having two reflection surfaces are individually disposed between the third lens groups and the imaging surface.

4. An endoscope objective optical system according to claim 3 that satisfies conditional expression (3):

$$fb/ihy>4 \qquad (3),$$

where fb is a distance from a final lens to an imaging surface, and ihy is a maximum image height in the direction of parallax.

* * * * *